United States Patent [19]
Yamamoto et al.

[11] Patent Number: 5,869,626
[45] Date of Patent: Feb. 9, 1999

[54] METAL-ENCAPSULATED FULLERENE COMPOUND AND A METHOD OF SYNTHESIZING SUCH COMPOUND

[75] Inventors: Kazunori Yamamoto, Naka-gun; Hideyuki Funasaka; Takeshi Takahashi, both of Hitachinaka; Takeshi Akasaka, Tsukuba; Tatsuhisa Kato, Okazaki; Shigeru Nagase, Hachiohji; Kaoru Kobayashi, Machida, all of Japan

[73] Assignee: Doryokuro Kakunenryo Kaihatsu Jigyodan, Tokyo, Japan

[21] Appl. No.: 606,941

[22] Filed: Feb. 26, 1996

[30] Foreign Application Priority Data

Aug. 31, 1995 [JP] Japan .................................... 7-223930

[51] Int. Cl.$^6$ .............................. C07F 5/00; C07F 7/22; C01F 1/00; C01B 31/00
[52] U.S. Cl. .............................. 534/10; 534/15; 534/16; 505/460; 423/445 B; 556/81
[58] Field of Search .................................... 534/10, 15, 16; 505/460; 423/DIG. 40, 445 B, DIG. 39; 556/81

[56] References Cited

U.S. PATENT DOCUMENTS 5,386,048  1/1995  West et al. .............................. 556/430

OTHER PUBLICATIONS

Marco Ciufolini, *Gendaikagaku*, No. 253, pp. 12–19, Apr. 1992.
Shigeru Yamago, *Kagaku*, vol. 50, pp. 12–16, Jun. 1995.
Simon Friedman et al., "Inhibition of the HIV–1 Protease by Fullerene Derivatives: Model Building Studies and Experimental Verification", *J. Am. Chem. Soc.*, No. 115, pp. 6506–6509, 1993.
Yan Chai et al., "Fullerenes with Metals Inside", *J. Phys. Chem.*, No. 95, pp. 7564–7568, 1991.
Koichi Kikuchi et al., "Isolation and Characterization of the Metallofullerene LaC$_{82}$", *Chemical Physics Letters*, vol. 216, No. 1,2, pp. 67–71, Dec. 24, 1993.
Toshiyasu Suzuki et al., "Electrochemical Properties of La@C$_{82}$", *J. Am. Chem. Soc.*, No. 115, pp. 11006–11007, 1993.
Kazunori Yamamoto et al., "Isolation of an ESR–Active Metallofullerene of La@C$_{82}$", *The Journal of Physical Chemistry*, vol. 98, pp. 2008–2011, No. 8, 1994.
Kazunori Yamamoto et al., "Isolation and Characterization of an ESR–Active La@C$_{82}$ Isomer", *J. Phys. Chem.*, vol. 98, pp. 12831–12833, 1994.
Toshiyasu Suzuki et al., Electrochemistry and Ab Initio Study of the La$_2$@C$_{80}$, *Angew. Chem. Int. Ed. Engl.*, vol. 34, No. 10, pp. 1094–1096, 1995.
Hisanori Shinohara et al., Encapsulation of a Scandium Trimer in C$_{82}$, *Nature*, vol. 357, pp. 52–54, May 7, 1992.
Hisanori Shinohara et al., Isolation and Spectroscopic Properties of Sc$_2$@C$_{74}$, Sc$_2$@C$_{82}$, and Sc$_2$@C$_{84}$, *J. Phys. Chem.*, vol. 97, pp. 4259–4261, 1993.

Hisanori Shinohara et. al., Spectroscopic Properties of Isolated Sc$_3$@C$_{82}$ Metallofullerene, *The Journal of Physical Chemistry*, vol. 98, No. 35, pp. 8597–8599, Sep. 1, 1994.
J.H. Weaver et al., "XPS Probes of Carbon–Caged Metals", *Chemical Physics Letters*, vol. 190, No. 5, pp. 460–464, Mar. 13, 1992.
Koichi Kikuchi et al., "Characterization of the Isolated Y@C$_{82}$", *J. Am. Chem. Soc.*, vol. 116, pp. 9367–9368, 1994.
Edward G. Gillan et al., "Endohedral Rare–Earth Fullerene Complexes", *J. Phys. Chem.*, vol. 96, pp. 6869–6871, 1992.
L. Moro et al., "Studies of Metallofullerene Primary Soots by Laser and Thermal Desorption Mass Spectrometry", *J. Phys. Chem.*, vol. 97, pp. 6801–6805, 1993.
Hideyuki Funasaka et al., "Magnetic Properties of Gd@C$_{82}$ Metallofullerene", *Chemical Physics Letters*, vol. 232, pp. 273–277, 1995.
Hideyuki Funasaka et al., "Magnetic Properties of Rare–Earth Metallofullerenes", *J. Phys. Chem.*, vol. 99, pp. 1826–1830, 1995.
Ting Guo et al., "Uranium Stabilization of C$_{28}$: A Tetravalent Fullerene", *Science*, vol. 257, pp. 1661–1664, Sep. 18, 1992.

(List continued on next page.)

Primary Examiner—Jose'G. Dees
Assistant Examiner—Michael G. Hartley
Attorney, Agent, or Firm—Oliff & Berridge, PLC

[57] ABSTRACT

A novel metal-encapsulated fullerene compound wherein a side chain is introduced in a metal-encapsulated fullerene is provided.

A metal-encapsulated fullerene compound represented by the following structural formula (1) is synthesized by causing a disilirane derivative or digermirane derivative having the following structural formula (2) to react with a metal-encapsulation fullerene so as to add functional groups to the fullerene.

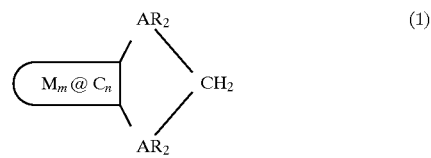

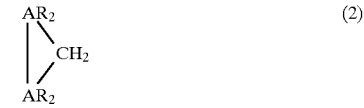

Herein, M is an encapsulated metal atom, m is an integer from 1 to 3, n is an even number from 28 to 200, and R is a t-butyl group or an aromatic group having alkyl groups in the 2,6-positions, such as mesityl, 2,6-diethylphenyl or 2,6-dimethylphenyl groups.

10 Claims, 7 Drawing Sheets

OTHER PUBLICATIONS

F.D. Weiss et al., "Photophysics of Metal Complexes of Spheroidal Carbon Shells", *J. Am. Chem. Soc.*, vol. 110, pp. 4464–4465, 1988.

L.S. Wang et al., "The Electronic Structure of $Ca@C_{60}$", *Chemical Physics Letters*, vol. 207, No. 4,5,6, pp. 354–359, May 28, 1993.

Lai–Sheng Wang et al., "Photoelectron Spectroscopy and Electronic Structure of $Ca@C_{60}$" *Supplement to Z. Phys.*, D 26, S297–299, 1993.

Harry R. Rose et al., "Calcium Inside $C_{60}$ and $C_{70}$ –From Coorongite, a Precursor of Torbanite", *J. Chem. Soc., Chem., Commun.*, pp. 941–942, 1993.

Harry R. Rose., "Endohedral Barium and Strontium Fullerenes", *J. Chem. Soc., Chem. Commun.*, pp. 1361–1363, 1993.

T. Pradeep et al., "A Novel $FeC_{60}$ Adduct in the Solid State", *J. Am. Chem. Soc.*, vol. 114, pp. 2272–2273, 1992.

T. Pradeep et al., "Investigations of Iron Adducts of $C_{60}$ Novel $FeC_{60}$ in the Solid State with Fe Inside the $C_{60}$ Cage", *Indian Journal of Chemstry*, vol. 31A&B, pp. F17–F21, May 1992.

D.S. Bethune et al., "Cobalt–Catalysed Growth of Carbon Nanotubes With Single–Atomic–Layer Walls", *Nature* vol. 363, pp. 605–607, Jun. 17, 1993.

Akasaka et al. *J. Am. Chem. Soc.*, vol. 116, pp. 2627–2628, Mar. 23, 1994.

Suzuki et al., *J. Am. Chem. Soc.*, vol. 116, pp. 1359–1363, Feb. 23, 1994.

Akasaka et al., *J. Am. Chem. Soc.*, vol. 115, pp. 10366–10367, Nov. 03, 1993.

(A) ESR spectrum of La@C$_{82}$. (B) ESR spectrum of the adduct(7).
(C) Simulated ESR spectrum of the adduct(7).

METAL-ENCAPSULATED FULLERENE COMPOUND AND A METHOD OF SYNTHESIZING SUCH COMPOUND

BACKGROUND OF THE INVENTION

1. Field of the Invention

This invention relates to a useful metal-encapsulated fullerene compound having application as a functional material, a superconducting material, an electronics material or a pharmaceutical material.

2. Description of the Related Art

An all-carbon fullerene is a recently discovered carbon allotrope typified by Buckminsterfullerene ($C_{60}$), and it has attracted attention in recent years because of its unique cage (shell) structure. After discovery of macroscopic preparations of all-carbon fullerenes in 1990, various physical and chemical properties of the fullerenes were clarified, and since many derivatives of all-carbon fullerene have now been synthesized, nowadays they are applied to electrical conductors, semiconductors and pharmaceutical products. Many reports about application of all-carbon fullerenes and their derivatives have appeared in the literature (Gendaikagaku, No. 253, April 1992, pp. 12–19, and Kagaku, Vol. 50, June 1995, pp. 12–16), and in particular, biological activity have emerged for derivatives of all-carbon fullerene (J. Am. Chem. Soc., 1993, Vol. 115, p. 6506) which have led to further research.

A metal-encapsulated fullerene is a new material closely related to an all-carbon fullerene. This material is comprised of an ordinary fullerene cage and a metal atom incorporated into inside of its shell structure. The physical and chemical properties of metal-encapsulated fullerenes can be controlled by changing their encapsulated elements, suggesting many potential applications. After the invention of a method for macroscopic synthesis of lanthanum-encapsulated fullerenes $La_m@C_n$ (R. Smalley et al., J. Phys. Chem. 1991, Vol. 95, p.7564), intensive research is now being carried out. According to Smalley's report, it is possible to produce one-lanthanum-encapsulated fullerenes $La@C_n$ with $n=36–122$, two-lanthanum-encapsulated fullerenes $La_2@C_n$ up to $n=110$, and three-lanthanum-encapsulated fullerenes $La_3@C_n$ up to $n=98$. Although there is essentially no higher limit, there is a lower limit for the value of n in $M_m@C_n$ fullerenes. And it is thought that the limit depends on the size and number of encapsulated metals or metal ions.

In the case of $La@C_{82}$, a method has been described for obtaining a pure sample and its characterizations have been reported (K. Kikuchi et al., Chem. Phys. Lett. 1993, Vol. 216, p. 67 and J. Am. Chem. Soc. 1994, Vol. 116, p. 9367; T. Suzuki et al., J. Am. Chem. Soc. 1993, Vol. 115, p. 11006; K. Yamamoto et al., J. Phys. Chem. 1994, Vol. 98, p. 2008 and J. Phys. Chem. 1994, Vol. 98, p. 12831). In the case of fullerenes encapsulating two lanthanum atoms, the characterization of $La_2@C_{80}$ has been reported (T. Suzuki et al., Angew. Chem. Int. Ed. Engl. 1995, Vol. 34, p. 1094).

The synthesis of scandium-encapsulated fullerenes, $Sc_m@C_n$ (m=1–3), is reported by H. Shinohara in Nature 1992, Vol. 357, p. 52. The separation methods are described for $Sc_2@C_n$ (n=74, 82, 84) in J. Phys. Chem. 1993, Vol. 97, p. 4259, and for $Sc_3@C_{82}$ in J. Phys. Chem. 1994, Vol. 98, p. 8597.

The first synthesis of yttrium-encapsulated fullerenes, $Y_m@C_n$, was reported by J. Weaver et al. (Chem. Phys. Lett. 1992, Vol. 190, p. 460), and the characterization of $Y@C_{82}$ was described by K. Kikuchi et al. in J. Am. Chem. Soc. 1994, Vol. 116, p. 9367.

The production and extraction of lanthanoid-encapsulated fullerenes, $M_m@C_n$ (M=Ce, Nd, Sm, Eu, Gd, Tb, Dy, Ho, Er) are described by R. L. Whetten et al. in J. Phys. Chem. 1992, Vol. 96, p. 6869, and the production of other lanthanoid-encapsulated fullerenes, $M_m@C_n$ (M=Pr, Eu, Yb, Lu) is reported by R. S. Ruoff et al. in J. Phys. Chem. 1993, Vol. 97, p. 6801. Of these, the isolation and characterization of $Gd@C_{82}$ were reported by H. Funasaka et al. in Chem. Phys. Lett. 1995, Vol. 232, p. 273 and J. Phys. Chem. 1995, Vol. 99, p. 1826.

As to an actinoid-encapsulated fullerene, the synthesis of uranium-encapsulated fullerenes $U_m@C_n$ (m=1–2, n=28–80) is reported by R. Smalley et al. in Science 1992, Vol. 257, p. 1661.

In the case of alkali-metal-encapsulated fullerenes, potassium and cesium have been reported. The production of potassium-encapsulated fullerenes, $K@C_n$, is reported by R. Smalley et al. in J. Am. Chem. Soc. 1988, Vol. 119, p. 4464, and of cesium-encapsulated fullerenes, $Cs@C_n$, by R. Smalley et al. (J. Am. Chem. Soc. 1988, Vol. 110, p. 4464).

Fullerenes encapsulating an alkaline earth metal have been reported for calcium, strontium and barium. The production and extraction of a calcium-encapsulated fullerene, $Ca@C_{60}$, was first performed by R. Smalley et al. (Chem. Phys. Lett. 1993, Vol. 207, p. 354 and Z. Phys. 1993, Vol. D26, p. 297), after which the production of other $Ca@C_n$ fullerenes was confirmed by K. J. Fisher et al. (J. Chem. Soc., Chem. Commun. 1993, 941). The production of strontium-encapsulated fullerenes, $Sr_m@C_n$, and barium-encapsulated fullerenes, $Ba_m@C_n$, was reported by K. J. Fisher et al. (J. Chem. Soc., Chem. Commun. 1993, 1361).

As an example of fullerenes encapsulating a transition metal, the synthesis of an iron-encapsulated fullerene, $Fe@C_{60}$, is reported by C. N. R. Rao et al. (J. Am. Chem. Soc. 1992, Vol. 114, p. 2272, and Indian J. Chem. 1992, Vol. 31, p. F17). The first synthesis of a cobalt-encapsulated fullerene, $Co@C_{60}$, is described by D. S. Bethune et al. in Nature 1993, Vol. 363, p. 605.

As described hereinabove, it has been reported that a variety of metal elements are encapsulated in fullerenes, most of the reports concern methods of their production, isolation and characterization. Since all-carbon fullerene derivatives have biological activity, various potential applications of metal-encapsulated fullerenes, such as biological activity, are now envisaged. In addition, in the case of missile therapy of cancer using radioactive elements, fullerenes encapsulating radioactive elements are expected to play an important role. When you test biological activity of a certain substance or use it in a treatment for cancer, its water solubility must be enhanced and its affinity for the organism must be increased. Therefore it is necessary to synthesize derivatives of metal-encapsulated fullerenes with hydrophilic groups in the same way as the case for all-carbon fullerenes. To date, however, no metal-encapsulated fullerene derivative has been successfully synthesized in test tube amounts, and its method of synthesis remains unclear. This is why there have so far been no reports for the biological activity of metal-encapsulated fullerene compounds, and why there have so far been no successful development and no synthesis of functional materials, semiconductor materials, electronics materials and pharmaceutical materials using these metal-encapsulated fullerenes or metal-encapsulated fullerene compounds at the present time.

DESCRIPTION OF THE PREFERRED EMBODIMENTS

This invention was conceived in view of the above problems. It aims to provide useful, novel metal-encapsulated fullerene compounds that may be used as functional materials, semiconducting materials, electronics materials or pharmaceutical materials, and a method of synthesizing such compounds.

After exhaustive studies, the inventors succeeded in synthesizing organic silicon derivatives and organic germanium derivatives of metal-encapsulated fullerenes, and thereby arrived at the present invention.

This invention is a metal-encapsulated fullerene compound having the following structure:

where

A is a silicon or germanium atom,

M is an encapsulated metal atom, m is an integer from 1 to 3, n is an even number from 28 to 200, and R is an organic group which protects and stabilizes a three-membered ring comprising two of the aforesaid A atoms and a methylene group.

This invention is characterized in that, in the aforesaid metal-encapsulated fullerene having the aforesaid structure (1), the aforesaid metal atom M is chosen from a group comprising lanthanoid elements, actinoid elements, transition elements, alkali metal elements and alkaline-earth metal elements.

This invention is further characterized in that, in the metal-encapsulated fullerene compound having the aforesaid structure (1), the organic group R is a t-butyl group or an aromatic group having substituents in the 2, 6-positions.

This invention is moreover a method of synthesizing metal-encapsulated fullerene compounds by adding functional groups to metal-encapsulated fullerenes, wherein a disilirane derivative or a digermirane derivative having the following structure is reacted with a metal-encapsulated fullerene.

Herein A is a silicon or a germanium atom, and R is an organic substituent group which protects and stabilizes a three-membered ring comprising two of the aforesaid A atoms and a methylene group.

The added group R in the three-membered ring compound (2), must be a functional group which protects and stabilizes the A—A bond in the three-membered ring compound used as a starting material, and it must therefore be a stereochemically bulky group. Moreover in the method of synthesizing metal-encapsulated fullerene compounds according to this invention, the group R is a stereochemically bulky alkyl group or aryl group. Typical examples of R are t-butyl, mesityl, 2,6-diethylphenyl and 2,6-dimethylphenyl groups, the last three aryl groups having substituents in the 2,6-positions.

To react the metal-encapsulated fullerenes $M_m@C_n$ with a disilirane or digermirane, in general, the fullerene and disilirane or digermirane are dissolved in a solvent in a quartz reaction tube, and after freeze degassing, they are reacted by irradiating with light. As irradiating light, light of 400 nm and longer wavelength from a halogen lamp is particularly effective (decomposition occurs using light of shorter than 400 nm wavelength). The reaction may however also be performed by heating in a reaction tube.

In the light-induced reaction, from 1 to 10 moles of disilirane or digermirane is used per mole of metal-encapsulated fullerene. The solvent used in this reaction may be an aromatic hydrocarbon solvent such as benzene, toluene, xylene or mesitylene, or a halogenated aromatic hydrocarbon solvent such as chlorobenzene, dichlorobenzene, trichlorobenzene or chloronaphthalene.

This invention is the first attempt to introduce a side chain into a metal-encapsulated fullerene. In the prior art, side chains have been introduced into all-carbon fullerenes, and there are metal-encapsulated fullerenes which do not have side chains, however no metal-encapsulated fullerenes having side chains had been prepared. In the case of introducing side chains into all-carbon fullerenes, light from the mercury lamp is used. But when the same method is applied to introduce side chains into metal-encapsulated fullerenes, these compounds decompose. This is due to the fact that ordinary light from the mercury lamp contains intense light component of shorter than 400 nm wavelength. However, by adding predetermined three-membered ring compounds under irradiation of light of 400 nm and longer wavelength, the side chains can be introduced. It may be expected that for this addition compound both addition across the 6-ring-6-ring junction and the 5-ring-6-ring junction can occur.

As described heretofore, a variety of metal-encapsulated fullerenes are already known. It will be understood that the metal-encapsulated fullerene compound of this invention can be applied to a fullerene encapsulating any metal. To put it simply, this invention contains a synthetic method of a corresponding addition product to a double bond. It is therefore evident that it may be applied not only to the metals listed in the embodiments described hereinbelow, but also to a fullerene encapsulating any of the metals cited in the literature.

BRIEF DESCRIPTION OF THE DRAWINGS

FIG. 2(A) is a diagram showing the electron spin resonance spectrum of the compound (3). FIG. 2(B) is the electron spin resonance spectrum of a mixture of $La@C_{82}$ and the compound (3). FIG. 2(C) is a diagram showing the electron spin resonance spectrum of $La@C_{82}$. In the figures, the horizontal axis is magnetic field intensity and the vertical axis is the differential of absorption intensity.

EXAMPLES 1–5

This invention will now be described in further detail with reference to the examples below.

EXAMPLE 1

Synthesis of $La@C_{82}(Mes_2Si)_2CH_2$ (Mes=mesityl), an organosilicon derivative of a lanthanum-encapsulated fullerene $La@C_{82}$ (5 mg) and disilirane $(Mes_2Si)_2CH_2$ (10 mg) were added to 1,2,4-trichlorobenzene (20 ml) in a quartz glass tube, after freeze degassing, the solution was irradiated with a halogen lamp for one hour at room temperature. Using a filter, light of 400 nm and shorter wavelength was cut off in the irradiation.

The color of the product solution did not change from yellowish brown of $La@C_{82}$ solution. Using high performance liquid chromatography with 1,2,4-trichlorobenzene as eluent, a reaction product could be separated from unreacted $La@C_{82}$. The reaction product obtained is apparently a 1:1 addition product (3) of disilirane and $La@C_{82}$, for which the formula is given below.

Figure 1:
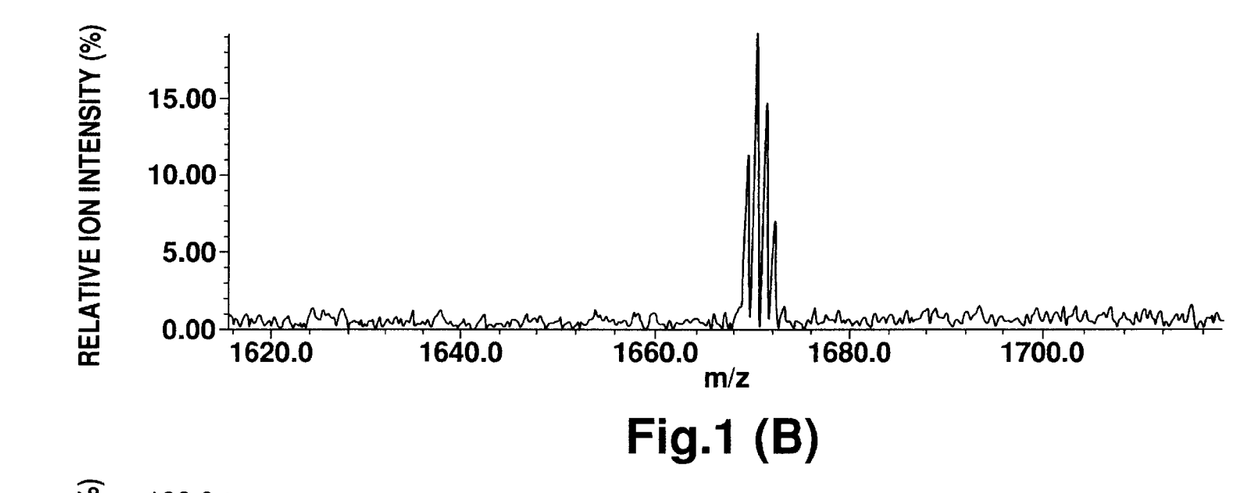
FIG. 1(A) is a diagram of the mass spectrum of a compound (3).
FIG. 1(B) is an enlarged view of the mass number region 1615–1740. In this figure, the horizontal axis is mass number and the vertical axis is relative ion intensity.

In the mass spectrum of the product, (FIG. 1(A), FIG. 1(B)), molecular ion peaks were seen from 1669 to 1672, and peaks due to fragmentation were found at 1123 to 1125. This confirms production of the compound (3). The electron spin resonance spectrum of the compound (3) (FIG. 2(A)) shows some eight equally spaced signal groups due to splitting by the lanthanum nucleus as in the case of the spectrum of $La@C_{82}$ (FIG. 2(C)), but their spacing is different. Also the presence of various signal groups in the spectrum (FIG. 2(A)) is thought to indicate that there are structural isomers of the adduct differing in the position of the disilirane.

Figure 2:
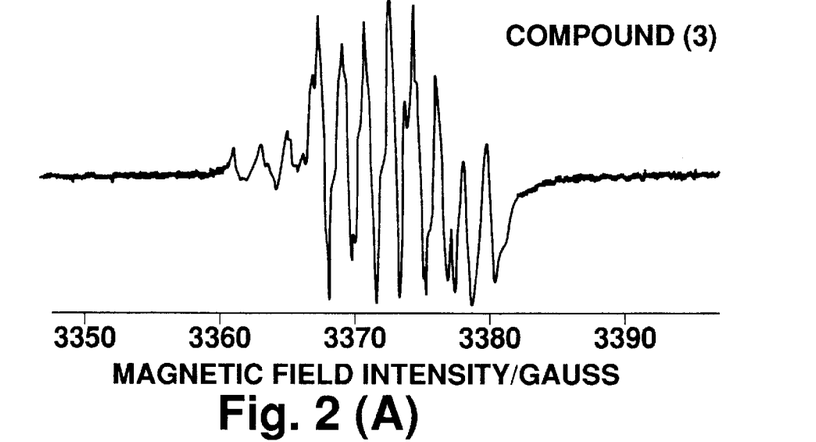

(3)

EXAMPLE 2

Synthesis of $Gd@C_{82}(Mes_aSi)_2CH_2$ (Mes=mesityl), an organosilicon derivative of a gadolinium-encapsulated fullerene $Gd@C_{82}$ (1 mg) and disilirane $(Mes_2Si)_2CH_2$ (2 mg) were added to 1,2,4-trichlorobenzene (2 ml) in a quartz glass tube, after freeze degassing, the solution was heated at 80° C. for 10 hours. As a result, a compound (4), a 1:1 addition product of disilirane and $Gd@C_{82}$, was obtained.

Figure 3:
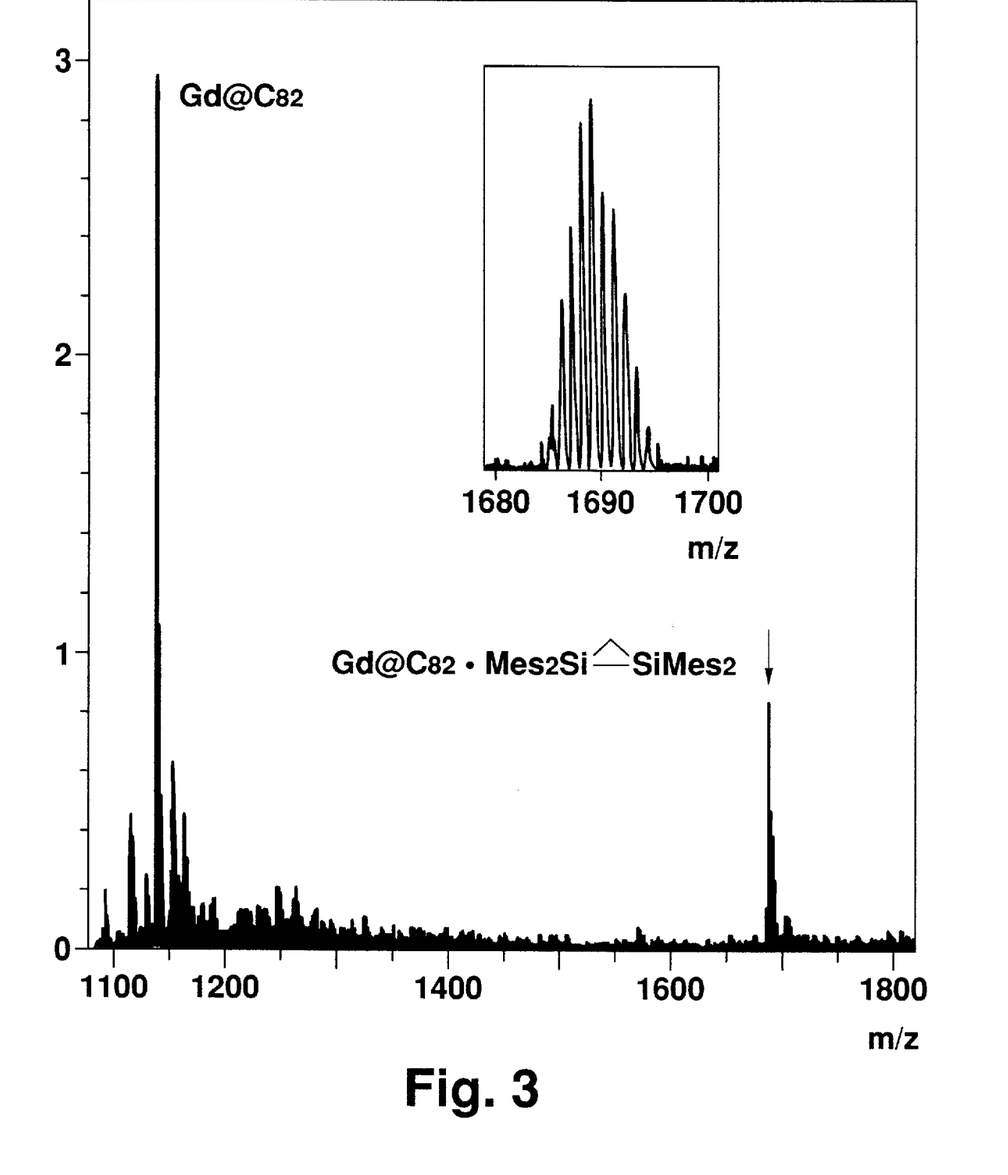
FIG. 3 is the mass spectrum of a compound (4). In the figure, the horizontal axis is mass number and the vertical axis is relative ion intensity.

In the mass spectrum of the product (FIG. 3), molecular ion peaks were found from 1685 to 1693 and peaks due to fragmentation were observed from 1139 to 1146, confirming the synthesis of the compound (4).

(4)

EXAMPLE 3

Synthesis of $La_2@C_{80}(Mes_2Si)_2CH_2$ (Mes=mesityl), an organosilicon derivative of a lanthanum-encapsulated fullerene $La_2@C_{80}$ (1 mg) and disilirane $(Mes_2Si)_2CH_2$ (2 mg) were added to 1,2,4-trichlorobenzene (2 ml) in a quartz glass tube, after freeze degassing, the solution was irradiated with a halogen lamp at room temperature. As a result, a compound (5), a 1:1 addition product of disilirane and $La_2@C_{80}$, was obtained.

Figure 4:
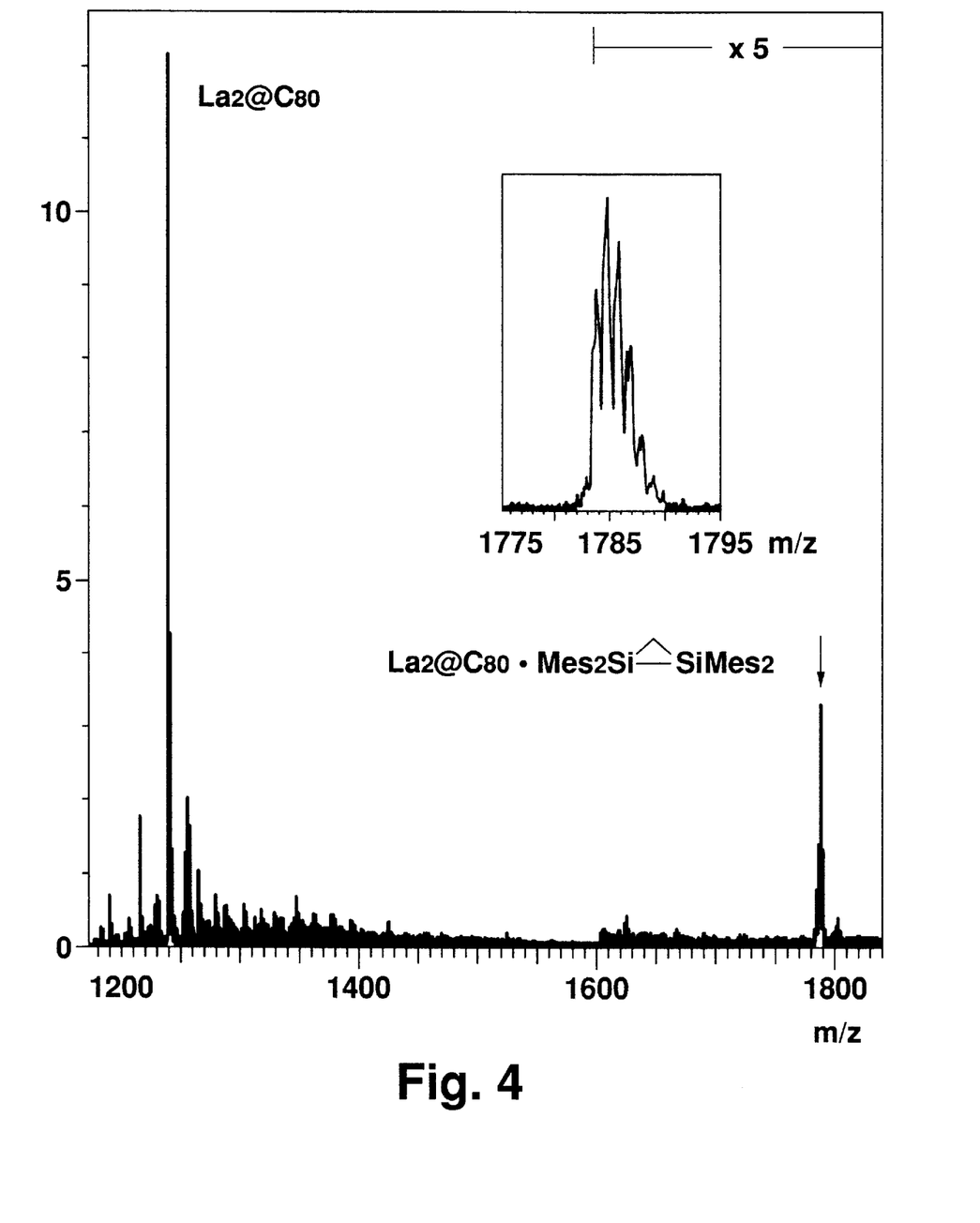
FIG. 4 is the mass spectrum of a compound (5). In the figure, the horizontal axis is mass number and the vertical axis is relative ion intensity.

In the mass spectrum of the product (FIG. 4), molecular ion peaks were found from 1784 to 1788, and peaks due to fragmentation were observed from 1238 to 1240, confirming the synthesis of the compound (5).

(5)

EXAMPLE 4

Synthesis of $Sc_2@C_{84}(Mes_2Si)_2CH_2$ (Mes=mesityl), an organosilicon derivative of a scandium-encapsulated fullerene $Sc_2@C_{84}$ (1 mg) and disilirane $(Mes_2Si)2CH_2$ (2 mg) were added to 1,2,4-trichlorobenzene (2 ml) in a quartz glass tube, after freeze degassing, the solution was irradiated with a halogen lamp at room temperature. As a result, a compound (6), a 1:1 addition product of disilirane and $Sc_2@C_{84}$, was obtained.

Figure 5:
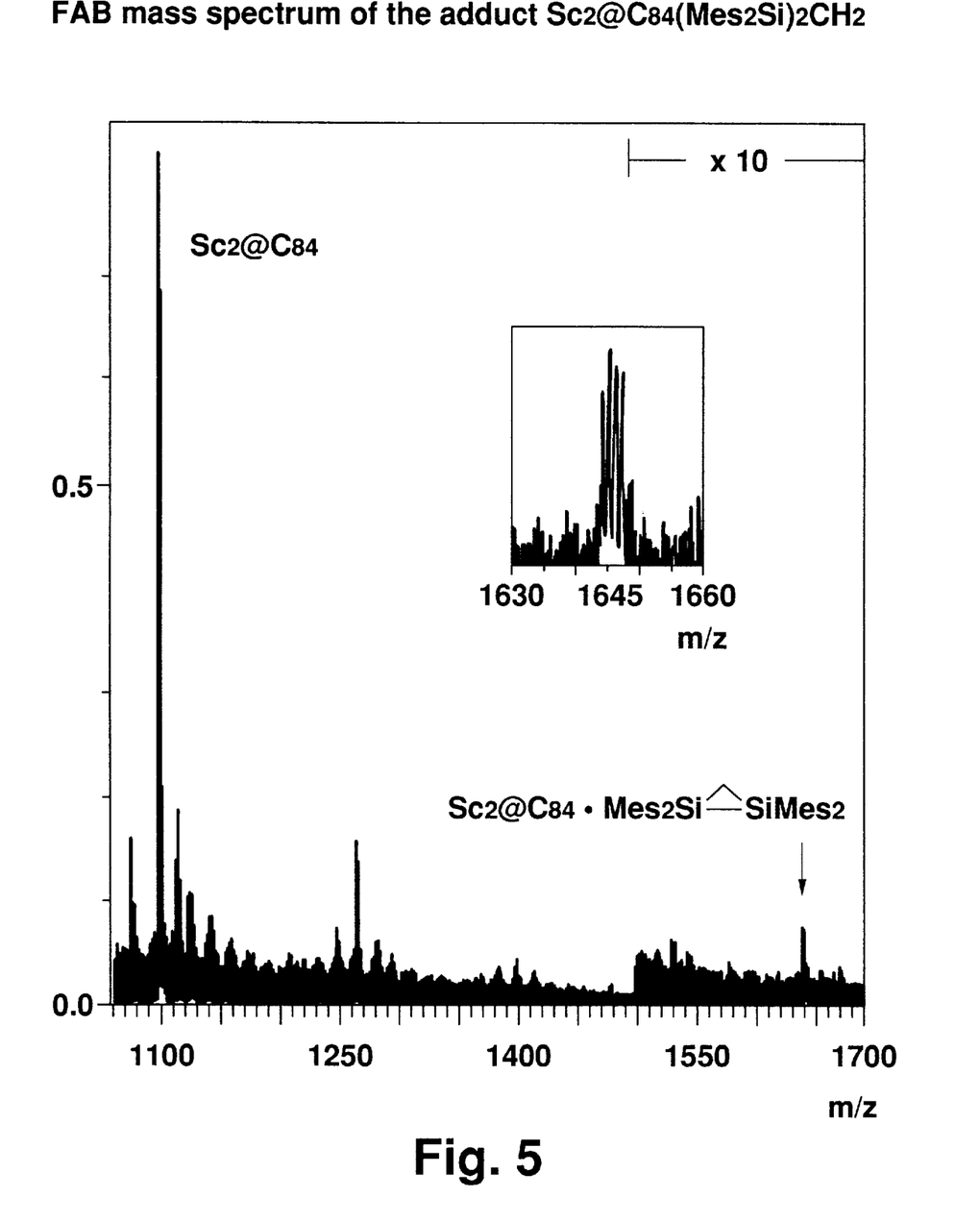
FIG. 5 is the mass spectrum of a compound (6). In the figure, the horizontal axis is mass number and the vertical axis is relative ion intensity.

In the mass spectrum of the product (FIG. 5), molecular ion peaks were found from 1644 to 1647, and peaks due to fragmentation were observed from 1098 to 1100, confirming the synthesis of the compound (6).

(6)

EXAMPLE 5

Synthesis of $La@C_{82}(Dep_2Ge)_2CH_2$ (Dep=2,6-diethylphenyl), an organogermanium derivative of a lanthanum-encapsulated fullerene $La@C_{82}$ (1 mg) and digermirane $(Dep_2Ge)_2CH_2$ (2 mg) were added to 1,2,4-trichlorobenzene (4 ml) in a quartz glass tube, after freeze degassing, the solution was heated at 50° C. for 30 minutes.

Figure 6:
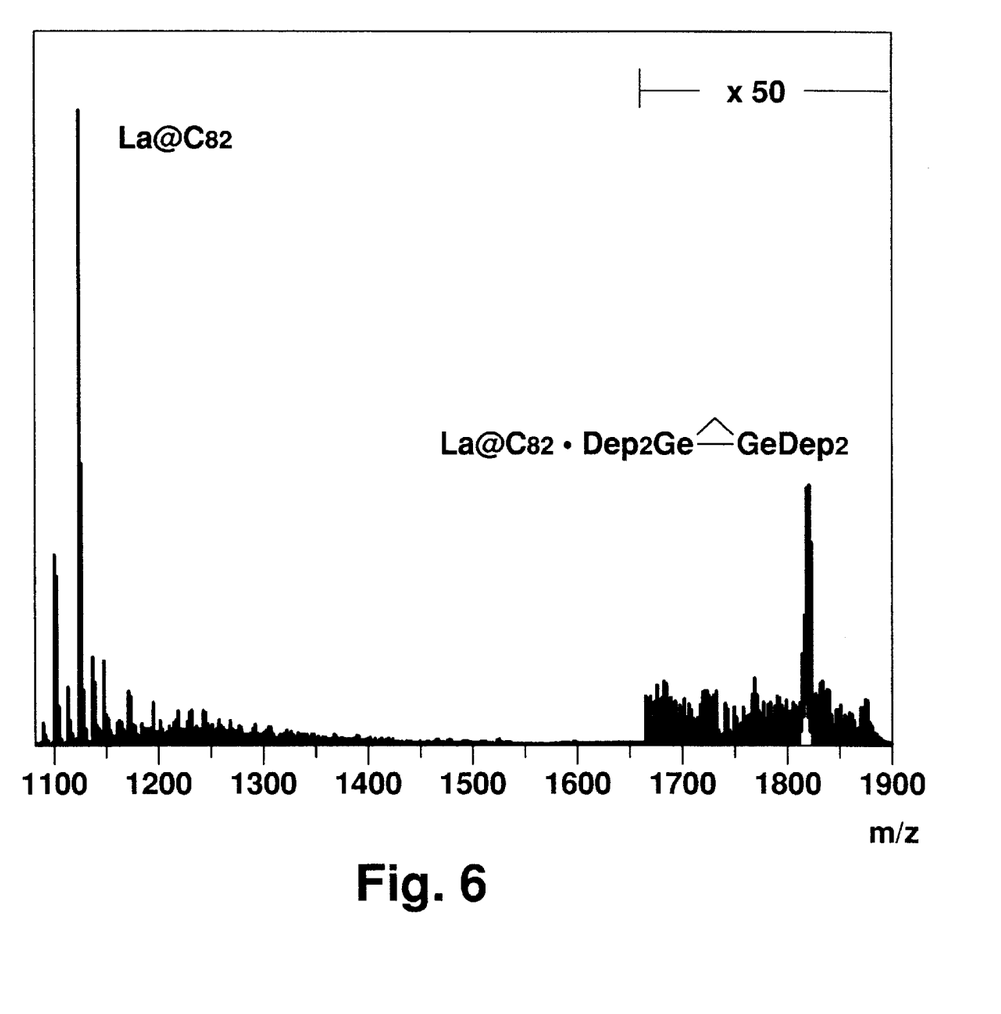
FIG. 6 is the mass spectrum of a compound (7). In the figure, the horizontal axis is mass number and the vertical axis is relative ion intensity.
Figure 7:
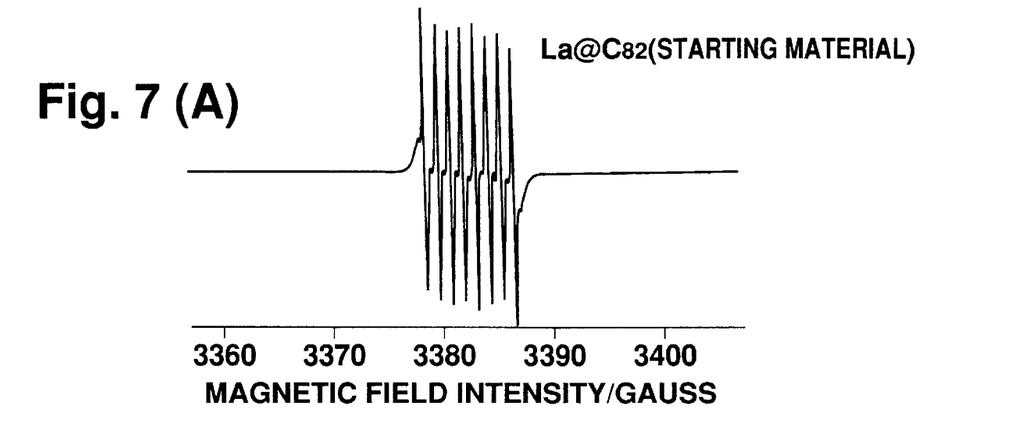
FIG. 7(A) is a diagram showing the electron spin resonance spectrum of $La@C_{82}$ (starting material).
FIG. 7(B) is a diagram showing the electron spin resonance spectrum of the compound (7).
FIG. 7(C) is a diagram showing the electron spin resonance spectrum of the compound (7) in a simulation.

In the mass spectrum of the product (FIG. 6), molecular ion peaks were found from 1809 to 1821 and peaks due to fragmentation were observed from 1123 to 1125, thereby confirming a resulting compound (7) to be a 1:1 addition product of digermirane and $La@C_{82}$. The electron spin resonance spectrum of the compound (7) (FIG. 7(B)) shows some eight equally spaced signal groups due to splitting with the lanthanum nucleus as in the case of the spectrum of $La@C_{82}$ (FIG. 7(A)), but their spacing is different. Because the presence of various signal groups in the spectrum (FIG. 7(B)) can be interpreted as a superposition of signals with different spacing and intensity (FIG. 7(C)), it appears that there are structural isomers of the adduct differing in the position of the digermirane.

Forms of the Invention

The metal-encapsulated fullerene compounds according to this invention may easily be introduced a variety of functional groups in the side chain. It may for example be expected that when carboxyl, hydroxyl or alkoxyl groups which have a strong affinity for living organisms are bonded to the side chain, the metal-encapsulated fullerene compound itself will have biological activity. If the encapsulated metal is gadolinium, the compound may be used as a magnetic resonance relaxant for MRI as in the case of other gadolinium chelate reagents. As a gadolinium ion is toxic, the problem of toxicity arises with gadolinium chelate reagents where the metal ion tends to dissociate easily, however with a metal-encapsulated fullerene there is no metal-ion dissociation so the problem does not occur.

Advantages of the Invention

According to this invention described hereinabove, a novel metal-encapsulated fullerene compound wherein a side chain is introduced into a metal-encapsulated fullerene can now be synthesized. It is expected that this novel metal-encapsulated fullerene compound will be useful as a functional material, superconducting material, electronics material or pharmaceutical material.

What is claimed:

1. A metal-encapsulated fullerene compound having the following structure:

where

A is a silicon or germanium atom,

M is an encapsulated metal atom, m is an integer from 1 to 3, $M_m@C_n$ represents a metal-encapsulated fullerene contained as part of said structure (1), n is an even number from 28 to 200, and R is an organic substituent selected from the group consisting of a stereochemically bulky alkyl group and a stereochemically bulky aryl group.

2. A metal-encapsulated fullerene compound as defined in claim 1 wherein:

said encapsulated metal atom M is at least one element selected from the group consisting of lanthanoid elements, actinoid elements, transition elements, alkali metal elements and alkaline-earth metal elements.

3. A metal-encapsulated fullerene compound as defined in claim 1 wherein:

said encapsulated metal atom M is a radioactive metal element.

4. A method of synthesizing a metal-encapsulated fullerene compound by adding functional groups to a metal-encapsulated fullerene, comprising reacting a disilirane derivative or digermirane derivative having the following structure (2)

with a metal encapsulated fullerene to produce said compound, wherein said compound has the following structure (1)

wherein in structure (1):

A is a silicon or germanium atom,

R is an organic substituent selected from the group consisting of a stereochemically bulky alkyl group and a stereochemically bulky aryl group, M is an encapsulated metal atom.

m is an integer from 1 to 3, $M_m@C_n$ represents a metal-encapsulated fullerene contained as a part of said structure (1), and n is an even number from 28 to 200, and wherein in structure (2):

A is a silicon or gennanium atom, and

R is an organic substituent selected from the group consisting of a stereochemically bulky alkyl group and a stereochemically bulky aryl group which protects and stabilizes the ring comprising two of said A atoms and the methylene bridge of said structure (2).

5. A method of synthesizing a metal-encapsulated fullerene compound as defined in claim 4, wherein a metal encapsulated in said metal-encapsulated fullerene is at least one element selected from the group consisting of lanthanoid elements, actinoid elements, transition elements, alkali metal elements and alkaline-earth metal elements.

6. A method of synthesizing a metal-encapsulated fullerene compound as defined in claim 4, wherein a metal encapsulated in said metal-encapsulated fullerene is a radioactive metal element.

7. A method of synthesizing a metal-encapsulated fullerene compound as defined in claim 4, wherein said metal-encapsulated fullerene compound and said disilirane derivative or digermirane derivative are dissolved in an aromatic hydrocarbon reaction solvent or a halogenated aromatic hydrocarbon reaction solvent.

8. A method of synthesizing a metal-encapsulated fullerene compound as defined in claim 4, further comprising:

dissolving said metal-encapsulated fullerene and said disilirane derivative or digermirane derivative in a reaction solvent to form a reactant solution, removing dissolved gas from said reactant solution by freeze degassing, and reacting said disilirane derivative or digermirane derivative with said metal-encapsulated fullerene by irradiating said reactant solution.

9. A method of synthesizing a metal-encapsulated fullerene compound as defined in claim 8, wherein said reacting is accomplished by irradiation with light having a wavelength of at least 400 nm.

10. A method of synthesizing a metal-encapsulated fullerene compound as defined in claim 4, further comprising:

dissolving said metal-encapsulated fullerene and said disilirane derivative or digermirane derivative in a reaction solvent to form a reactant solution, removing dissolved gas from said reactant solution by freeze degassing, and heating said reactant solution to react said disilirane derivative or digermirane derivative with said metal-encapsulated fullerene in said reactant solution.

* * * * *